(12) United States Patent
Kvitnitsky et al.

(10) Patent No.: US 7,892,581 B2
(45) Date of Patent: Feb. 22, 2011

(54) COMPOSITIONS AND METHODS FOR PROTECTION OF HARVESTED FRUITS FROM DECAY

(75) Inventors: Emma Kvitnitsky, Kiryat Shmona (IL); Ruth Ben-Arie, Metula (IL); Irina Paluy, Upper Galilee (IL); Olga Semenenko, Kiryat Shmona (IL)

(73) Assignee: Gavish-Galilee Bio Applications Ltd., Kiryat Shmona (IL)

( * ) Notice: Subject to any disclaimer, the term of this patent is extended or adjusted under 35 U.S.C. 154(b) by 508 days.

(21) Appl. No.: 11/814,889

(22) PCT Filed: Jan. 26, 2006

(86) PCT No.: PCT/IL2006/000111
§ 371 (c)(1),
(2), (4) Date: Jul. 26, 2007

(87) PCT Pub. No.: WO2006/080013
PCT Pub. Date: Aug. 3, 2006

(65) Prior Publication Data
US 2008/0131533 A1   Jun. 5, 2008

Related U.S. Application Data

(60) Provisional application No. 60/646,604, filed on Jan. 26, 2005.

(51) Int. Cl.
*A61K 36/54* (2006.01)
(52) U.S. Cl. .................................................. 424/739
(58) Field of Classification Search .................. None
See application file for complete search history.

(56) References Cited

U.S. PATENT DOCUMENTS

| | | | |
|---|---|---|---|
| 5,639,794 A * | 6/1997 | Emerson et al. | 514/699 |
| 5,703,124 A | 12/1997 | Takata et al. | |
| 6,361,812 B1 | 3/2002 | Ekanayake et al. | |
| 2002/0099101 A1 * | 7/2002 | Emerson et al. | 514/729 |
| 2003/0185946 A1 | 10/2003 | Il et al. | |
| 2006/0134239 A1 * | 6/2006 | Weide et al. | 424/745 |

FOREIGN PATENT DOCUMENTS

| | | |
|---|---|---|
| EP | 1106070 A2 | 6/2001 |
| GB | 1465533 | 2/1977 |
| JP | 2003144065 A | 5/2003 |
| KR | 20020004918 A | 1/2002 |
| WO | 9620595 A1 | 7/1996 |
| WO | 9620596 A1 | 7/1996 |
| WO | 9853707 A1 | 12/1998 |
| WO | 03028451 A2 | 4/2003 |

OTHER PUBLICATIONS

Moleyar et al.,"Antifungal activity of some essential oil components", Food Microbiology, 3:331-336 (1986).
Utama et al.,"In Vitro Efficacy of Plant Volatiles for Inhibiting the Growth of Fruit and Vegetable Decay Microorganisms", J Agric. Food Chem, (50) 6371-6377 (2002).
Reddy et al.,"Characterization and Use of Essential Oil From *Thymus vulgaris* Against *Botrytis cinerea* and *Rhizopus stolonifer* in Strawberry Fruits" Photochemistry. vol. 47, 8:1515-1520,(1998.
International Search Report and Written Opinion mailed Jul. 23, 2007.

* cited by examiner

*Primary Examiner*—Christopher R Tate
*Assistant Examiner*—Deborah A. Davis
(74) *Attorney, Agent, or Firm*—Browdy and Neimark, PLLC

(57) ABSTRACT

Methods and compositions comprising essential oils or components thereof for protecting harvested fruits against decay caused by a specific pathogenic fungus are provided, such as Cinnamon cassia oil for protection of persimmons against *Alternaria alternata*, strawberries against *Botrytis cinerea*, or mandarins against *Penicillium italicum* or *Penicillium digitatum*.

10 Claims, 8 Drawing Sheets

COMPOSITIONS AND METHODS FOR PROTECTION OF HARVESTED FRUITS FROM DECAY

FIELD OF THE INVENTION

The present invention relates to compositions and methods for the protection of harvested fruits against decay. In particular, the invention relates to the application of essential oils or components thereof to protect harvested fruits against pathogenic fungi.

BACKGROUND OF THE INVENTION

Annual post-harvest spoilage of highly perishable agricultural commodities such as fruits has been estimated to result in losses in the range of 20-50% of the crop worldwide, depending on the sophistication of available storage facilities.

Fruits are generally susceptible to rapid post-harvest degradation due to high respiration rates and microbial spoilage. Upon harvesting, fruits undergo enzymatic breakdown, becoming soft or shriveled. This is regarded as normal post-harvest deterioration and is acceptable up to a certain level. Unacceptable post-harvest deterioration is the occurrence of diseases caused mainly by fungi, which require a special antifungal treatment. Synthetic fungicides are currently the main agents for controlling post-harvest wastage due to pathogenic fungi and have been used extensively for decades.

Post-harvest treatments aimed at delaying deterioration include washing, waxing, curing, plant growth regulators, sprout inhibitors, disinfectants, irradiation, controlled ripening, controlled de-greening, light (minimal) processing, and chemical treatments.

Chemical treatments to reduce post-harvest decay have only become of significant use in the last 30 years. The success of these treatments depends on the initial spore load, the time that passes from infection to treatment, the depth of the infection within the host tissues, the growth rate of the infection, temperature and relative humidity, and the depth at which the chemical can penetrate the host tissues.

In addition, the applied chemical must not be phytotoxic, must comply with local food additive laws and must have established maximum residual limits (MRLs). Chemicals may be impregnated into wraps, box liners, applied as fumigants, solutions and suspensions, or in wax.

Most of the post-harvest treatments currently available are aimed at treating citrus fruits, pome fruits such as apples, pears or quinces, and melons or bananas. Very little success has been reported in treating soft fruits such as strawberries, raspberries, or grapes, and persimmons or peaches.

Today, the agricultural industry uses a variety of post-harvest antifungal treatments based on synthetic chemicals, to avoid or delay disease and prolong the shelf life of fresh produce. However, fungicide-tolerant strains, e.g. *Botrytis* spp., *Penicillium* spp., are present in most packing houses, rendering synthetic fungicides less effective or totally ineffective (Spotts et al, 1986).

Another problem concerning the use of synthetic fungicides is the fact that they leave residues, which may be considered carcinogenic and/or environmentally hazardous.

In addition, in the organic agriculture sector no post-harvest treatment is applied, as no product currently meets the stringent standards of international organic growers' associations. With the ever-increasing popularity of organically grown produce, there is an urgent demand to supply this sector with an acceptable treatment that will lengthen the storage and shelf life of fresh agricultural produce.

The potential for post-harvest application of synthetic fungicides is limited also by both adverse effects due to wetting of the fruits and stringent regulations concerning the use of currently available fungicides. This issue has contributed to an urgent and significant need to develop alternative, safe, environmentally benign, and effective methods for controlling post-harvest pathogens, capable of complementing, or even completely replacing synthetic fungicides.

Biological control methods, involving a range of different approaches, including strengthening the commodity's natural defense mechanisms and application of antagonistic microorganisms and natural antimicrobial substances, have become popular in recent years.

Naturally occurring biologically active secondary metabolites from plants are examples of antimicrobial and antifungal compounds and may offer a new and effective solution for control of post-harvest diseases of horticultural products.

Essential oils, a class of volatile oils extracted from plants, fruits or flowers by steam, distillation or solvent extraction, are known to possess antimicrobial activity. Extensive work is being carried out around the world on essential oils and their components for several purposes: as pharmaceuticals for the drug industry or for non-conventional natural therapy, for cosmetic purposes; in agriculture, as pesticides or for preservation of foodstuff and agricultural produce.

Numerous essential oils produced by different genera are endowed with allelopathic, antimicrobic, antioxidant and/or bioregulatory properties (Deans et al, 1992; Piccalgia et al, 1993). The use of essential oils as antifungal agents in post-harvest storage is very promising owing to their negligible toxicity to mammals. In addition, due to their high degree of volatility, they can be used in active packing or in cold storage. Both the Council of Europe's Committee of Experts on Flavoring Substances and the FDA have not recommended limits on the use of essential oils. Furthermore, essential oils and their components have been evaluated by the US Flavoring Extract Manufacturers Association (FEMA) as GRAS (Generally Regarded As Safe).

The pesticidal activity of essential oils or components thereof in general is known from the literature and several essential oils have been proposed for use as plant pesticides. The fungicidal or fungistatic activity of essential oils in general is known from the literature for the protection and preservation of foodstuff (e.g. bread, meat), cereals (e.g. wheat) and agricultural commodities (Wilson et al, 1987).

Prior studies concern mainly in vitro testing (under ideal conditions) of essential oils or their components against fungi known to cause damage to fruits. Only a small number of studies have tested essentials oils in vivo (under commercial conditions) in post-harvested fruits and vegetables.

Different essential oils exhibit different fungicidal and fungistatic activity. In vitro, each essential oil is active against some types of fungi and is not active against others. Different essential oils may be active against the same pathogen, but at different concentrations. In vivo, the essential oil may be active against a certain pathogen in one type of fruit, but not against the same pathogen in a different fruit, or at least not at the same concentration.

The actual mode of action of essential oils is not fully known, although it is speculated to involve membrane disruption of pathogenic fungi by the lipophilic compounds (Bennis et al, 2004). Essential oils cause degeneration of the fungal hyphae, which are emptied of their cytoplasmic content (Zambonelli et al, 1994.) Destruction of the fungal hyphae prevents the spread of mycelia into new tissue, while the sporangia cannot sporulate to form new infective spores. Spores that have already spread and are dormant, awaiting favorable conditions for germination, may also be affected in the same way (Lambert et al, 2001).

The biological activity of the essential oils is evidently due to synergistic action of their components. Complex mixtures of the individual components (mostly monoterpenes and sesquiterpenes) in the oils are far more potent as a barrier to pathogen adaptation than the individual component (Carlton et al, 1992).

Some post-harvest pathogens have a limited host range. For instance, *Penicillium digitatum* attacks only citrus fruits and causes a green mold. Other pathogens are omnivorous and have a wide host range. Omnivorous fungi include *Alternaria alternata, Botrytis cinerea*, and *Rhizopus* spp., etc. All these fungi are economically important pathogens of a wide range of fruits.

Currently, green mold of citrus, caused by *Penicillium digitatum*, is controlled by applying synthetic fungicides such as imazalil and thiabendazole. Black spot decay of persimmon fruits is caused by *Alternaria alternata*, which attacks the developing fruits, but infections remain quiescent until after harvest, when the symptoms become apparent following prolonged storage at low temperature. A postharvest dip in a hypochlorite solution provides a certain degree of control (Prusky et al., 2001), but only storage using modified atmosphere packaging (MAP) has resulted in a sufficient delay in fungal development (Ben-Arie et al., 1991). MAP also decreases strawberry fruits decay caused by *Botrytis cinerea* but contributes to off-odors and flavors (Shamalia et al., 1992). Effective chemical control of *Rhizopus* rot in peaches is provided by dichloran. But its use was discontinued due to visible residues on the fruits. Moreover, the widespread use of chemicals in commercial packing houses has led to the proliferation of resistant strains of many pathogens (Palou et al, 2001).

Recent research has focused on the search for novel compounds active against these fungi, which may have potential in disease control. Some natural compounds have already been identified. Caccioni and Guizzardi (1994) reported that several oil extract components inhibited germination and growth of a wide range of fruits and vegetable post-harvest pathogenic fungi. Oil extracts from oregano (*Thymus capitatus*) (Arras et al., 1995); sage (*Salvia officinalis*) (Carta et al., 1996); marjoram (*Oreganum syriacum*), lavender (*Lavandula angustifolia*), lemongrass (*Cymbopogon citratus*), tea tree (*Melaleuca alternifolia*), melissa (*Melissa officinalis*), peppermint (*Mentha piperita*), penny royal (*Mentha pulegium*), jasmine (*Jasminum grandiflorum*), bois de rose (*Rosa* spp.), neroll (*Citrus aurantum*), wintergreen (*Gaultheria procumbens*) and hyssop (*Hyssopus officinalis*) (Cutler et al., 1996), all inhibited in vitro mycelial growth of *Botrytis cinerea*. However, the efficacy of these extracts may differ in in vivo systems under the influence of environmental conditions. Phytotoxicity problems may arise when these extracts are applied in liquid form to living fruit tissues.

Several publications and patents disclose the use of essential oils for food preservation. Japanese Publication No. JP59132876 discloses the use of a mixture of ethyl alcohol and an essential oil, essential oil component, spice or spice component such as allyl mustard oil, or beefsteak plant oil supported on a carrier such as non-woven cloth and zeolite, for food products and vegetable preservation inside a container that is sealed with a non-permeable material.

Japanese Publication No. JP58101670 discloses the use of a volatile substance with preservative effect such as ethyl alcohol, an organic acid or an essential oil, on a pouch made of a macromolecular continuous film with controlled permeability, for food preservation, wherein the pouch and the food product are packed together and sealed tightly. Japanese Publication No. JP58063348 describes vegetables that can be protected from microbial deterioration by adsorbing a substance such as an essential oil on zeolite, and packing the vegetables with the resulting zeolite. Japanese Publication No. JP8205768 discloses the use of thymol or Thyme essential oil for preservation of freshness of mushroom. No pathogens are mentioned.

Moldovian Patent No. MD682 discloses the use of *Origanum heracleoticum* essential oil (0.4-0.5%) in mixture with ethanol (99.5-99.6%) for protection of fruits (grapes) from decay caused by pathogenic fungi.

Japanese Publication No. JP10179104 discloses the use of one or more essential oils (cinnamon, garlic, thyme, oregano) for preservation of food (bread, dairy, fish, cakes, etc.), also against pathogenic fungi.

PCT Publication WO 00/21364 describes essential oils from plant species of the families Labiatae or Umbelliferae (e.g. *Origanum, Thymbra, Pinpinella*) that protect plants from insects, fungi, nematodes and bacteria when applied to the soil, leaves, etc.

U.S. Pat. No. 5,958,490 describes the use of activated carbon impregnated with essential oils and benzaldehyde, to provide controlled release of volatiles for the control of post-harvest disease. Neither pathogens, nor essential oils are specified.

U.S. Pat. No. 6,482,455 discloses the use of a composition consisting of the association of thymol, eugenol and cinnamaldehyde and an oligosaccharide, for the control of post-harvest pathogens of fruits and vegetables, applied in solid form (incorporated into the wax) or in a diluted dip. No pathogens are mentioned.

The efforts for finding essential oils for protection of fruits from pathogenic fungi without blemishing the fruits or affecting their taste and aroma have not been successful as yet.

SUMMARY OF THE INVENTION

In one aspect, the present invention provides a composition comprising an essential oil or components thereof for protecting harvested fruits against decay caused by pathogenic fungi, said composition being selected from:

(i) a composition comprising Cinnamon cassia (*Cinnamomum cassia* Presl.) oil or components thereof for protection of persimmons against *Alternaria alternata*, strawberries against *Botrytis cinerea*, or mandarins against *Penicillium italicum* or *Penicillium digitatum*;

(ii) a composition comprising Mustard (*Brassica nigra*) oil or components thereof for protection of persimmons against *Alternaria alternata*, strawberries against *Botrytis cinerea*, or mandarins against *Penicillium italicum* or *Penicillium digitatum*;

(iii) a composition comprising Thyme (*Thymus vulgaris*) oil or components thereof for protection of strawberries against *Botrytis cinerea* or peaches against *Rhizopus stolonifer*;

(iv) a composition comprising Nutmeg (*Myristica fragrans*) oil or components thereof for protection of strawberries against *Botrytis cinerea*;

(v) a composition comprising *Eucalyptus citriodora* (*Eucalyptus citriodora* Hook) oil or components thereof for protection of peaches against *Rhizopus stolonifer* or strawberries against *Botrytis cinerea*.

In another aspect, the present invention provides a method for protecting fruits against a pathogenic fungus that causes post-harvest decay in said fruits, which consists of treating the fruits after harvest with a composition of the invention comprising an essential oil or components thereof as described above.

BRIEF DESCRIPTION OF THE FIGURES

FIG. 2A is a graph showing the inhibitory effect of Mustard essential oil (M-1) (4 ppm) or Cinnamon cassia oil (CC-1) (20 ppm) on the percentage of decay caused by Alternaria alternata in inoculated persimmons stored at 20° C. for up to 39 days. FIG. 2B is a photograph showing the inhibitory effect of Mustard oil (M-1) (4 ppm) on development of decay in persimmons inoculated with Alternaria alternata after storage at 20° C. for 33 days.

FIG. 3A is a graph showing the inhibitory effects of Mustard essential oil (4 ppm) and Nutmeg oil (10 ppm) on the percentage of intact berries inoculated with Botrytis cinerea during storage at 4° C. for up to 31 days. FIG. 3B is a photograph showing the inhibitory effect of Cinnamon cassia oil (CC-1) at a concentration of 10 ppm (1) or 20 ppm (2) on decay development in strawberries inoculated with Botrytis cinerea, after storage at 4° C. for 31 days.

FIG. 4A is a graph showing the inhibitory effect of Eucalyptus citriodora essential oil (EC-1) at a concentration of 0.4 ppm (incubation for 3 or 24 h) or 2 ppm (incubation for 3 h) on the percentage of decay caused by Rhizopus stolonifer in inoculated peaches stored at 20° C. for up to 9 days. FIG. 4B is a photograph showing the effect of Thyme oil at a concentration of 0.2 ppm or 0.4 ppm on the inhibition of decay development in peaches inoculated with Rhizopus stolonifer and stored at 20° C. for 14 days.

FIG. 5A is a graph showing the inhibitory effect of Mustard essential oil (M-1) (4 ppm) or Cinnamon cassia oil (CC-1) (20 ppm) on the percentage of decay in mandarins infected with Penicillium italicum and stored at 4° C. for up to 9 days. FIG. 5B is a photograph showing the inhibitory effect of Mustard essential oil (M-1) on decay development in mandarins inoculated with Penicillium italicum and stored at 20° C. for 9 days.

FIG. 7A shows the release of allyl isothiocyanate, a main marker component of Mustard essential oil, into vapor phase. FIG. 7B shows release of the main marker components of Thyme essential oil (para-cymene, linalool, camphene and thymol) into vapor phase. FIG. 7C shows the release of the main marker components of Nutmeg essential oil (alpha-pinene, sabinene and beta-pinene) into the vapor phase. FIG. 7D shows the release of the main marker components of Eucalyptus citriodora essential oil (citronellal, alpha-pinene, beta-pinene and isopulegol) into vapor phase.

DETAILED DESCRIPTION OF THE INVENTION

Figure 1:
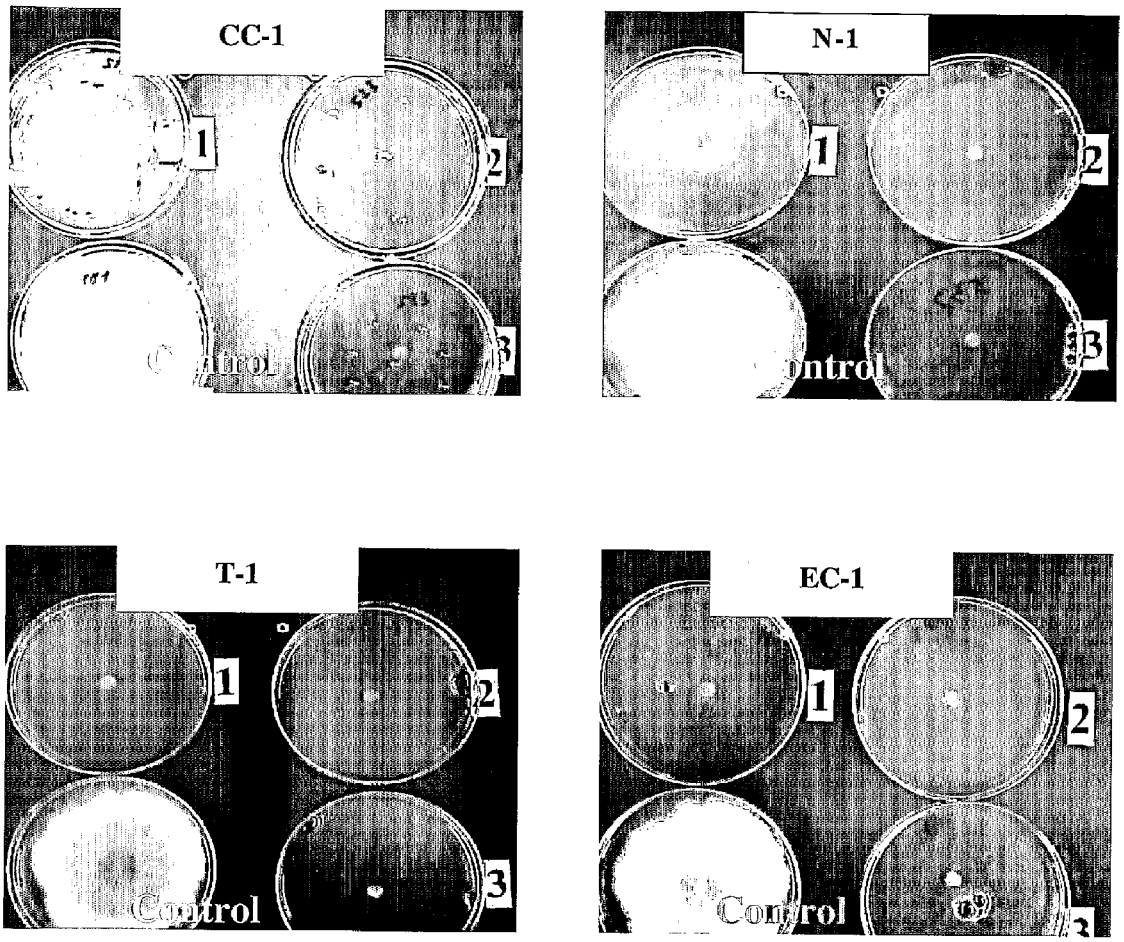
FIG. 1 shows the inhibition of growth of Botrytis cinerea by Cinnamon cassia oil (CC-1), Nutmeg oil (N-1), Thyme oil (T-1) and Eucalyptus citriodora oil (EC-1) in a Petri dish system at different concentrations of the essential oils: (1) 71.4 ppm; (2) 357 ppm; (3) 714 ppm; and a control (untreated Petri dishes).

The present invention provides compositions comprising natural compounds that can markedly delay post-harvest decay development in fruits and thus represent an attractive alternative to synthetic chemicals used today. Several potent specific essential oils that dramatically extend the shelf life of produce under high humidity and temperature conditions, without blemishing the fruit or affecting its taste and smell, have been identified according to the present invention and characterized. Since the compositions are natural products, they are promising candidates for use as Generally Recognized As Safe (GRAS) alternatives.

As used herein, the terms "green volatile" and "essential oil" are used interchangeably and refer to an essential oil of natural origin. The fungicidal effectiveness of a green volatile is determined herein for specific host-pathogen system(s) i.e., a fungus or a small number of closely related fungi, per fruit and per concentration. Statistically valid tests have shown that the identified essential oils, at minimal concentrations, could be instrumental in suppressing fungal pathogenic growth in persimmons, strawberries, peaches and mandarins, without having a detrimental effect on their aroma, color, texture and flavor, and without being phytotoxic to the treated fruit.

Although the fungicidal effect of some essential oils is known, the effective doses reported in the literature cannot be applied to harvested fruits due both to their phytotoxicity and their effect on the aroma and flavor of the treated produce.

It has been found, according to the present invention, that if a certain essential oil exhibits fungicidal activity against a phytopathogenic fungus in vitro, it will not necessarily protect any fruit from decay caused by said fungus. It is still necessary to test the essential oil in vivo on harvested fruits inoculated or liable to be infected by said phytopathogenic fungus, in order to establish that said essential oil will protect said fruits from decay caused by said fungus and will not have any detrimental effects on the form, aroma and flavor of the fruits.

The composition and antifungal effect of an essential oil can vary drastically due to differences between varieties and individual plants, the growing and environmental conditions of the plant and the extraction procedures used. Moreover, the composition of an essential oil from the same origin may vary even from batch to batch produced by the same manufacturer.

According to the present invention, several essential oils were tested and found to be effective for protection of persimmons, strawberries, mandarins and peaches against the fungi Botrytis cinerea, Rhizopus stolonifer, Alternaria alternata, Penicillium digitatum, and Penicillium italicum, that are responsible for post-harvest diseases in said fruits. Each fruit species was inoculated with the specific pathogen of greatest economic importance.

The present invention thus provides, in one embodiment, a composition comprising Cinnamon cassia oil or components thereof for protection of harvested persimmons against decay caused by Alternaria alternata. In another embodiment, a composition comprising Cinnamon cassia oil or components thereof is provided for protection of harvested strawberries against decay caused by *Botrytis cinerea*. In a further embodiment, a composition comprising Cinnamon cassia oil or components thereof is provided for protection of harvested mandarins against decay caused by *Penicillium italicum* or *Penicillium digitatum*.

In another embodiment, the present invention provides a composition comprising Mustard essential oil or components thereof for protection of harvested persimmons against decay caused by *Alternaria alternata*. In a further embodiment, a composition comprising Mustard essential oil or components thereof is provided for protection of harvested strawberries against decay caused by *Botrytis cinerea*. In still another embodiment, a composition comprising Mustard essential oil or components thereof is provided for protection of harvested mandarins against decay caused by *Penicillium italicum* or *Penicillium digitatum*.

In yet another embodiment, the present invention provides a composition comprising Thyme oil or components thereof for protection of harvested strawberries against decay caused by *Botrytis cinerea*. In a further embodiment, a composition comprising Thyme oil or components thereof is provided for protection of harvested peaches against decay caused by *Rhizopus stolonifer*.

In still another embodiment, the present invention provides a composition comprising Nutmeg oil or components thereof for protection of harvested strawberries against decay caused by *Botrytis cinerea*.

In yet a further embodiment, the present invention provides a composition comprising *Eucalyptus citriodora* oil or components thereof for protecting harvested peaches against decay caused by *Rhizopus stolonifer*. In a further embodiment, a composition comprising *Eucalyptus citriodora* oil or components thereof is provided for protection of harvested strawberries against decay caused by *Botrytis cinerea*.

In a further aspect, the present invention relates to a method for protecting fruits against a pathogenic fungus that causes post-harvest decay in said fruits, which comprises treating the fruits after harvest with a composition of the invention comprising an essential oil or components thereof as described above.

In another embodiment, the present invention relates to a method for extending the shelf-life of harvested fruits infected or liable to be infected by phytopathogenic fungi, which consists of applying a composition comprising said essential oil or components thereof to the harvested fruits, as described above.

According to the present invention, samples of the essential oils from different sources and batches were analysed, and the concentration ranges of each oil's components that were found essential for its protective activity against decay caused by different fungi in different fruits were determined, and their organoleptic properties were identified. These components are herein designated "marker components" and the ranges defined herein are those shown in the present experiments to exhibit superior performance. The compositions containing essential oils or components thereof, of course, include additional components and ingredients.

We have characterized essential oils from various manufacturers and marker components thereof and determined the profile of their release into vapor phase, during a period of 24 hours. It was interesting to note that the main marker component of, for example, Thyme oil-thymol (17.0-55.0% in oil) was discovered within 3 hours in the vapor phase at a low concentration (~1.2%), whereas p-cymene, which is present in the essential oil in a relatively low concentration (7.0-12.0%), was detected within 3 hours at a concentration of ~56%. A very similar pattern was also observed for other essential oils, except for Eucalyptus citriodora oil and Mustard essential oil. Furthermore, a strong correlation was observed between the composition of an essential oil in the liquid phase, well-defined marker components in the vapor phase, and its efficacy in controlling pathogenic fungi. In in vitro experiments, most of the single components applied individually did not evince strong antifungal activity. This indicates that a synergistic effect of individual marker components in the vapor phase exists and that the mode of action of an essential oil in the vapor phase may differ from the mode of action upon direct contact of the essential oil with the pathogenic fungi, and might be explained as a trigger to the self-defense system in the host fruit.

Thus, in one preferred embodiment of the invention, the Cinnamon cassia oil comprises at least the following marker components: cinnamic aldehyde (60.0-98.0%), cinnamyl acetate (1.0-4.0%), methoxycinnamic aldehyde (0.5-15.0%), linalool (0.3-8.0%), beta-caryophyllene (0.2-6.0%), alpha-pinene (0.2-1.0%), dl-limonene (0.2-1.5%), and camphene (0.1-0.7%).

In another preferred embodiment of the invention, the Thyme oil comprises at least the following marker components: thymol (17.0-55.0%), carvacrol (0.5-5.5%), alpha-pinene (0.5-5.5%), 1.8-cineol (0.5-4.5%), alpha-terpineol (0.7-15.0%), camphene (0.5-6.5%), beta-pinene (0.2-1.5%), p-cymene (7.0-12.0%), and linalool (1.0-30.0%).

In a further preferred embodiment of the invention, the Nutmeg oil comprises at least the following marker components: alpha-pinene (9.0-37.0%), beta-pinene (6.0-22.0%), sabinene (6.0-13.0%), myristicin (0.5-9.5%), dl-limonene (1.0-9.5%), and terpinen-4-ol (0.3-6.0%).

In yet another preferred embodiment of the invention, the *Eucalyptus citriodora* oil comprises at least the following marker components: citronellal (43.0-82.0%), (+)-citronellol (2.0-5.0), isopulegol (1.5-4.0%), alpha-pinene (0.2-1.5), beta-pinene (0.2-1.0%), and neoisopulegol (0.2-4.0%).

In still yet another preferred embodiment of the invention the Mustard essential oil comprises the following marker component: allyl isothiocyanate (58.0-98.0%), 3-butenyl isothiocyanate (0.5-1.5%), and diallyl sulfide (1.0-4.0%).

According to a preferred embodiment of the present invention, the compositions comprising the essential oils are applied without direct contact with the fruits. In one most preferred embodiment, the composition of the invention is applied in a volatile form. Application of the composition in a volatile form can be directly achieved by vaporizing the essential oil into the atmosphere surrounding the fruits. For example, it may be sufficient to place a sheet of paper that has been dipped in the essential oil in the storage room or in the fruits containers, in order to achieve the protective effect in bulk storage. This technique, besides conferring safety, is significantly more cost effective than current techniques since the fruits can be treated in bulk by application of an extremely low concentration of an essential oil. Alternatively, air can be passed over a remote source of the essential oil and circulated around the fruits. Other application techniques include, but are not limited to, impregnation of the essential oil into the packaging material itself, or incorporation of the essential oil into a slow release vehicle or carrier, for example, by encapsulation or placement in a closed permeable container, film or sachet. However, any other form of application that might be suitable such as a spray or an aqueous emulsion or any other form for protecting fruits during transportation and storage, are encompassed by the present invention.

The methodology of the present invention can be summarized by the following steps:

(i) Screening of samples of raw material essential oils and determination of their analytical data;

(ii) Chemical characterization of the essential oils (liquid state) by using tandem gas chromatography (GC)/mass spectrometer (MS) methods;

(iii) In vitro validation of the essential oil activity against different phytopathogenic fungi in dose-response experiments;

(iv) Organoleptic tests;

(v) Chemical characterization of the vapor phase of the essential oils and determination of their profile of release by using Headspace Gas Chromatography methods;

(vi) In vivo validation of the essential oil activity on fruits inoculated with fungi;

(vii) Statistical analysis and selection of the essential oils for use in the invention.

The results obtained according to the present invention clearly demonstrate the great potential of the identified essential oils for application in vaporized form for post-harvest fruits protection. The natural volatile compounds selected did not show any organoleptic and/or phytotoxic impact on the fruits tested and did not have detrimental effects on the fruit's aroma and/or flavor. The compositions of the invention are not toxic and can be used easily and safely for protection of fruits against phytopathogenic fungi.

The invention will now be illustrated by the following non-limiting examples.

EXAMPLES

Materials and Methods (i) Essential oils and individual components thereof. The essential oils used in the present invention were: Cinnamon cassia oil (Florasynth Inc. NY, USA; Tamar Shivuk, Israel), Mustard essential oil (Synth, India; Spectrum Chemical and Laboratory products, USA), Nutmeg essential oil (Plant Lipids Ltd, India; Tamar Shivuk, Israel), Thyme oil (Roth, Germany; Tamar Shivuk, Israel), and *Eucalyptus citriodora* oil (R. C. Treatt Florida, USA; Tamar Shivuk, Israel). The determination of marker components and their concentration range in the essential oils was performed by GC-MS (gas chromatograph-mass spectrometer) analyses using GC/MS tandem Hewlett Packard 5890 Series II Plus Gas Chromatograph—HP 5972 Series—MSD, equipped with column HP-5 MS of volume 30 m×0.25 mm×0.25 µm.

The individual components of essential oils used were: alpha-pinene, beta-pinene, alpha-terpineol, cineol, p-cymene, thymol, carvacrol, cinnamic aldehyde, o-methoxycinnamic aldehyde, cinnamyl acetate, allylisothiocyannate, and citronellal (Aldrich Chem Co), dl-limonene and (+)-citronellol (Aromor, Israel).

The profile of release of essential oils was determined by analyses using Gas Chromatograph HP6890 Series GC-System (FID) coupled with HP 7694 Headspace sampler, equipped with column HP-5 Trace Analysis (5% PH Me Siloxane) of volume 30 m×0.25 mm×0.25 µm, at ambient temperature. The following model system was developed and calibrated: filter paper (Whatman No. 1) strips absorbed with appropriate volume of essential oil to achieve desired concentrations, i.e., similar to those used for in-vivo experiments, were placed in 20 ml and 100 ml vials. The vials were hermetically sealed and marked to indicate the time course of vaporization (1, 3, 14 and 24 hours). These vials were kept in the dark at a temperature of 20° C. until their gas chromatography analyses.

(ii) Tested fungi. The fungi used in the experiments were: *Botrytis cinerea, Rhizopus stolonifer, Alternaria alternata, Penicillium digitatum* and *Penicillium italicum*. All the fungi were isolated from the appropriate fruits and the isolates were cultured for 2-3 weeks on Potato Dextrose Agar medium (PDA, Difco Laboratories, Detroit, Mich., USA) at 25° C.

(iii) Tested fruits. The tested fruits, mature and healthy persimmons, strawberries, mandarins, and peaches, were obtained from local farms or markets in Israel. The strawberries used in the experiments were organically grown. Each fruit species was inoculated with a characteristic pathogenic fungus of economic importance.

(iv) In vitro screening of essential oils and individual components thereof. The technique was based on the volatile properties of tested essential oils or individual components thereof. A sterilized filter paper strip (Whatman No. 1; 0.5 cm×1 cm) was centered on the inside of a glass Petri dish lid. Mycelial discs (~0.8 cm diameter) of the fungi (*Alternaria alternata, Botrytis cinerea* or *Rhizopus stolonifer*), were placed on potato-dextrose-agar (PDA) medium in the center of sterilized Petri dishes. To test the growth inhibition of *Penicillium* strains, suspensions of *Penicillium italicum* or *Penicillium digitatum* were prepared at a concentration of ~$10^4$ spores/ml and 0.1 ml of the suspension was uniformly spread, using a Drigalski spatulum, onto PDA medium in Petri dishes. Essential oils (6-60 µl) or individual components thereof were applied to the filter paper, the dishes were tightly sealed to avoid gas exchange and the compounds were allowed to evaporate. The dishes were incubated in a reversed position at 25° C. in the dark. All experiments were performed in triplicate with a negative control. The negative control was prepared by adding 60 µl water to the filter paper. Colony diameter or the number of colonies (for *Penicillium*) were measured after 5-10 days, depending on the fungal species. Colony area was calculated based on colony diameter with the area of the initial mycelial disc subtracted. Percent inhibition of fungal growth was calculated as the ratio of the colony diameter, after subtracting the diameter of the initial disc, and the colony diameter of the control.

(v) In vivo testing of essential oils. The concentration of pathogenic fungus spore suspension for fruits inoculation was $10^6$ spores/ml in all cases. The peel of the fruit at the inoculation site was disinfected with 96% ethanol and equidistant circles were marked and numbered on the fruit equator (in persimmons, four equidistant circles were marked on the flat distal end). To simulate a wound infection, the fruits (peaches and persimmons) were punctured at the inoculation site with a 0.5 mm needle to a depth of 5 mm, then 10 µl of spore suspension were applied using a pipette, and the fruits were allowed to dry for 1 hour. In mandarins each inoculation site was wounded with a 0.5 mm needle that had been dipped in the spore suspension, to a depth of 5 mm. Strawberries were dipped for inoculation in the specific spore suspension without wounding. The fruits were then placed in polypropylene (PP, food grade) containers. A sterilized filter paper disk (Whatman No. 1; 2 cm in diameter) was attached to the inside of the container cover. The tested essential oil was added, in liquid form, to the filter paper disk at a final concentration range of 0.4-20 ppm, depending on the type of essential oil. The container was sealed immediately to avoid volatile escape and the essential oil was allowed to evaporate for 3-48 hours at 4-20° C. Inoculated fruits sealed in a container without the presence of essential oils, were used as the negative control. RH (relative humidity) in all tests was 65-90%. The temperature varied depending on the type of fruits. After this treatment, the fruits were stored in slightly opened containers for 7-39 days.

(vi) Evaluation of decay in inoculated fruits and statistical analysis. The area of decay on the fruits was calculated as percentage of the total fruit area. The diameter of the infected area was measured at specific times during storage. Decay on strawberries was evaluated by calculating the percentage of rotten berries.

Statistical analysis—Analysis of variance (ANOVA) was conducted using the SPSS statistical package. Data are the averages of at least 30 single fruits replications.

(vii) Organoleptic tests. Organoleptic testing includes color, flavor, texture, and aroma. Taste comparisons are conducted using a panel of judges trained to evaluate taste and aroma. For evaluation of taste results, a coarse scale ranging from 1 to 2 was specified to indicate in general terms the occurrence of change in taste and aroma, wherein 1 stands for an original taste, similar to control, and 2 for a strong altered taste. A second finer scale of from 1 to 5 also served to estimate the taste, wherein: 1. Excellent; 2. Good; 3. Just acceptable/average/moderate or neutral; 4. Poor; and 5. Inedible. The organoleptic tests were performed in one session on all fruits tested at a certain time point.

Example 1

In Vitro Screening of Essential Oils

Screening of essential oils and individual components thereof was carried out in order to evaluate their in vitro activity in inhibiting the growth of the pathogenic fungi. The isolated plant pathogenic fungi: *Botrytis cinerea, Rhizopus stolonifer, Alternaria alternata, Penicillium digitatum* and *Penicillium italicum*, were grown on Petri dishes in the presence of different concentrations of the essential oils. As shown in FIG. 1, Cinnamon cassia oil (CC-1), Nutmeg oil (N-1), Thyme oil (T-1) and *Eucalyptus citriodora* (EC-1) oil at different concentrations: 1. 71.4 ppm; 2. 357 ppm; and 3. 714 ppm, significantly inhibited the growth of *Botrytis cinerea* in comparison with control (untreated Petri dish). The concentration in ppm is defined herein as the volume in μl of essential oil loaded on the filter paper per volume of the Petri dish in liters (μl/L).

Tables 1-5 summarize the percentage of inhibition of growth of various fungi in vitro by Cinnamon cassia, Thyme, Nutmeg, *Eucalyptus citriodora* and Mustard essential oils, respectively.

Cinnamon cassia oil, Mustard oil, Nutmeg oil, Thyme oil and *Eucalyptus citriodora* oil gave rise to at least 70% inhibition of a specific pathogen growth, in vitro, at a concentration of 357 ppm, and were thus considered potent and selected as candidates for further in vivo studies. The in vitro analysis of the selected oils was followed by organoleptic tests to determine their effect on color, texture taste and aroma of the treated fruit. Even a slight change in aroma, taste or texture of the treated fruits resulted in disqualification of the treatment oil. Thus, essential oils that were actually used for treatment against decay were only those that were found both potent in the in vitro tests and passed the organoleptic tests.

TABLE 1

Inhibition of growth of various fungi by Cinnamon cassia oil

| | Concentration of oil (μl/L) | | |
|---|---|---|---|
| Fungus | 71.4 | 357 | 714 |
| *Botrytis cinerea* | 10% | 100% | 100% |
| *Alternaria alternata* | 50% | 100% | 100% |
| *Rhizopus stolonifer* | 10% | 100% | 100% |
| *Penicillium italicum* | 100% | 100% | 100% |
| *Penicillium digitatum* | 100% | 100% | 100% |

TABLE 2

Inhibition of growth of various fungi by Thyme oil

| | Concentration of oil (μl/L) | | |
|---|---|---|---|
| Fungi | 71.4 | 357 | 714 |
| *Botrytis cinerea** | 100% | 100% | 100% |
| *Rhizopus stolonifer* | 10% | 100% | 100% |
| *Penicillium italicum* | 30% | 100% | 100% |
| *Penicillium digitatum* | 50% | 100% | 100% |

*At lower concentrations of 11.9 and 35.7 ppm, inhibition was 80 and 85% respectively

TABLE 3

Inhibition of growth of various fungi by Nutmeg oil

| | Concentration of oil (μl/L) | | |
|---|---|---|---|
| Fungi | 71.4 | 357 | 714 |
| *Botrytis cinerea** | 60% | 100% | 100% |
| *Rhizopus stolonifer* | 60% | 100% | 100% |
| *Penicillium italicum* | 10% | 10% | 10% |
| *Penicillium digitatum* | 0% | 60% | 80% |

*At an intermediate concentration of 178.5 ppm, inhibition was 95%

TABLE 4

Inhibition of growth of various fungi by *Eucalyptus citriodora* oil

| | Concentration of oil (μl/L) | | |
|---|---|---|---|
| Fungi | 71.4 | 357 | 714 |
| *Botrytis cinerea** | 100% | 100% | 100% |
| *Alternaria alternata* | 60% | 90% | 100% |
| *Rhizopus stolonifer* | 100% | 100% | 100% |
| *Penicillium italicum* | 40% | 10% | 100% |
| *Penicillium digitatum* | 50% | 70% | 100% |

*At a lower concentration of 35.7 ppm, inhibition was 60%

TABLE 5

Inhibition of growth of various fungi by Mustard essential oil

| | Concentration of oil (μl/L) | | | |
|---|---|---|---|---|
| Fungi | 35.7 | 71.4 | 357 | 714 |
| *Botrytis cinerea* | 100% | 100% | 100% | 100% |
| *Alternaria alternata* | 50% | 100% | 100% | 100% |
| *Rhizopus stolonifer* | — | 100% | 100% | 100% |
| *Penicillium italicum* | — | 100% | 100% | 100% |
| *Penicillium digitatum* | — | 100% | 100% | 100% |

Example 2

**Low Doses of Mustard Essential Oil or Cinnamon Cassia Oil Significantly Reduce Black Spot Disease Caused by *Alternaria alternata* in Persimmons**

Persimmons (10 replicates of 10 fruits per container) inoculated with *Alternaria alternata* (four infection sites inoculated with 10 μl suspension, $10^6$ spores/ml, on each fruit), were incubated with Mustard essential oil (4 ppm) or Cinnamon cassia oil (20 ppm) for 3 hours in sealed containers, and thereafter stored in the same slightly opened containers for up to 39 days at 20° C. Inoculated persimmons not treated with the essential oils were used as control.

Figure 2A:
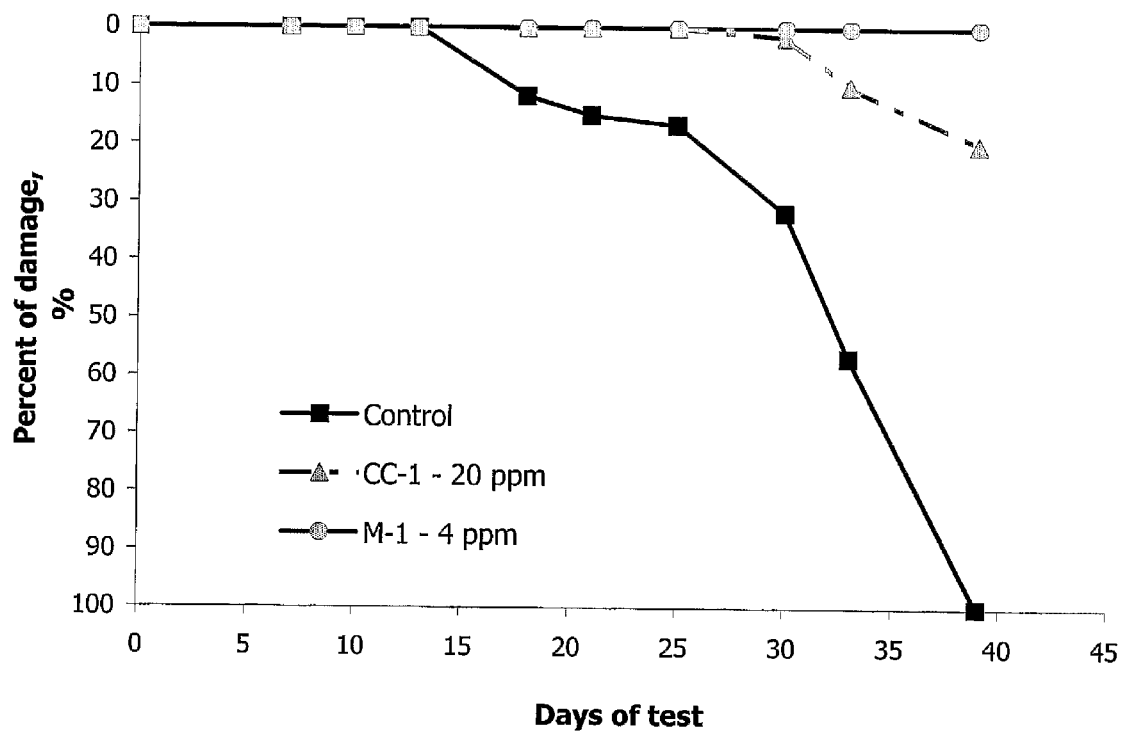
FIGS. 2A-2B show the effect of Mustard essential oil (M-1) or Cinnamon cassia oil (CC-1) on decay development in persimmons inoculated with Alternaria alternata ($10^6$ spores/ml).
Figure 2B:
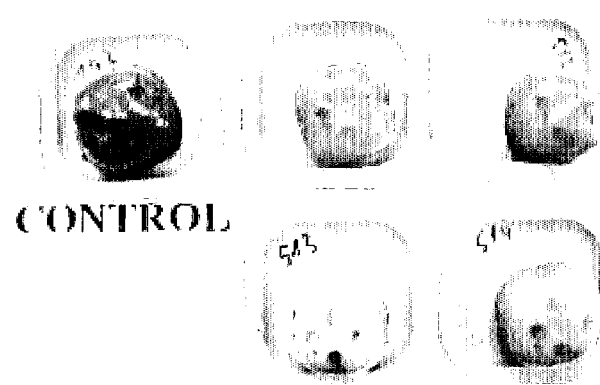

As shown in FIG. 2A, Cinnamon cassia oil (20 ppm) and Mustard essential oil (4 ppm) reduced the *Alternaria alternata* rot on persimmons by 80% and 100%, respectively, during 39 days storage at 20° C. The significant inhibitory effect of Mustard oil (M-1) on the development of decay in persimmons inoculated with *Alternaria alternata* and stored at 20° C. for 33 days, is shown in FIG. 2B.

Example 3

**Low Doses of Mustard Essential Oil, Nutmeg Oil or Cinnamon Cassia Oil Significantly Reduce Decay Caused by Grey Mould (*Botrytis cinerea*) in Strawberries**

Strawberries (10 replicates of 10 fruits per container) were inoculated with *Botrytis cinerea* ($10^6$ spores/ml), incubated in sealed containers with Mustard essential oil (1-4 ppm), Nutmeg oil (1-10 ppm) or Cinnamon cassia oil (1-20 ppm) for 3 hours and stored in the same slightly opened containers for up to 34 days at 4° C. or for up to 7 days at 20° C. Inoculated strawberries not treated with the essential oils were used as control.

Figure 3A:
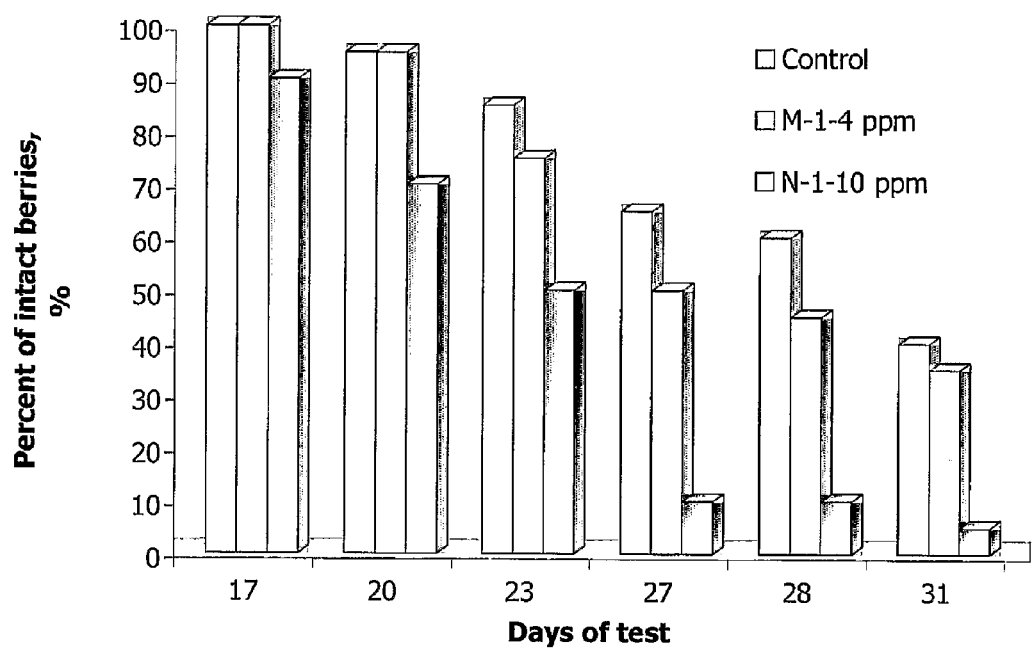
FIGS. 3A-3B show the effect of Mustard essential oil (M-1) Cinnamon cassia oil (CC-1) or Nutmeg oil (N-1) on decay development in strawberries inoculated with Botrytis cinerea ($10^6$ spores/ml).
Figure 3B:
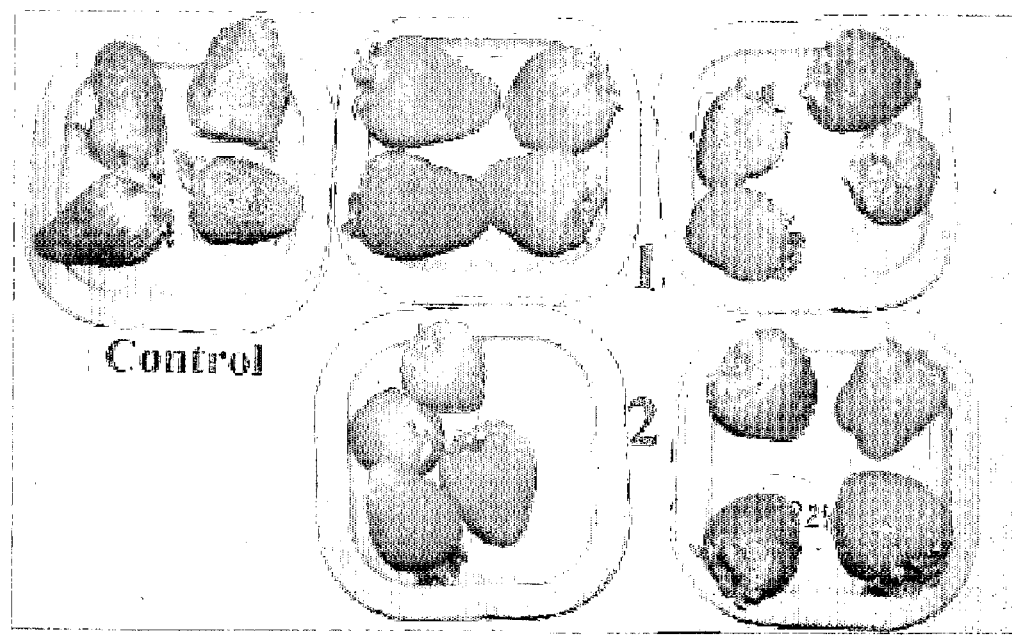

As shown in FIG. 3A, *Botrytis cinerea* decay on strawberries was suppressed by 40% following incubation with a low dose of Nutmeg oil (10 ppm) (4° C., 28 days). Significantly reduced decay was also achieved by applying a low dose of Mustard essential oil (4 ppm) (4° C., 31 days). The effect of Cinnamon cassia oil at two different concentrations (10 ppm and 20 ppm) on inhibition of decay development in strawberries inoculated with *Botrytis cinerea* and stored at 4° C. for 31 days is shown in FIG. 3B.

Example 4

**Low Doses of *Eucalyptus citriodora* Oil or Thyme Oil Significantly Reduce Decay Caused by *Rhizopus* (*Rhizopus stolonifer*) in Peaches**

Peaches (10 replicates of 10 fruits per container) were inoculated with *Rhizopus stolonifer* (four inoculation sites with 10 μl suspension at $10^6$ spores/ml on each fruit), incubated with *Eucalyptus citriodora* (0.4-2 ppm) or Thyme oil (0.2-0.4 ppm) for 3-24 hours in sealed containers and stored in the same slightly opened containers for up to 30 days at 20° C. Inoculated peaches, not treated with the essential oils, were used as control.

Figure 4A:
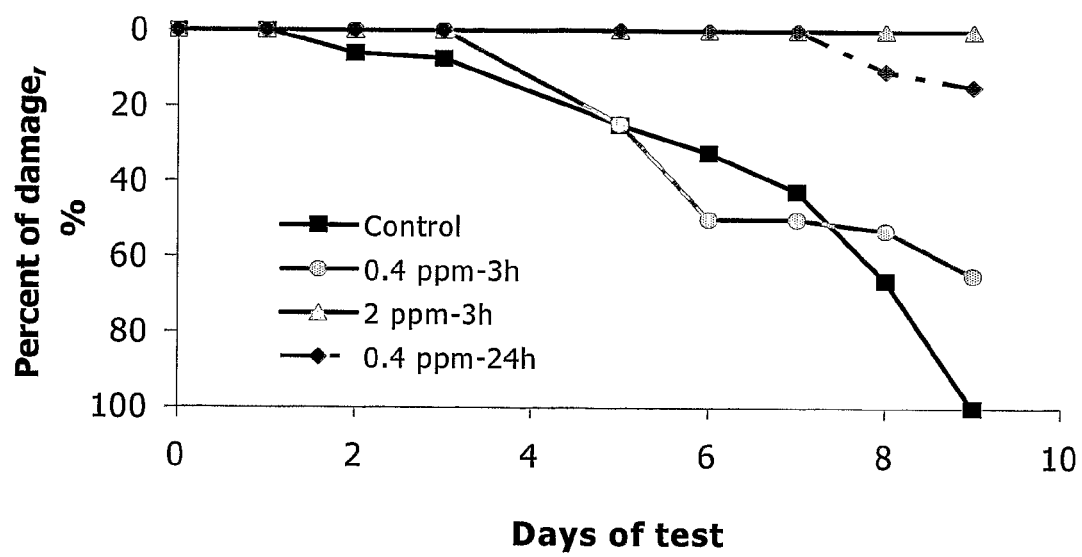
FIGS. 4A-4B show the effect of Eucalyptus citriodora (EC-1) and Thyme essential oils on decay development in peaches inoculated with Rhizopus stolonifer ($10^6$ spores/ml).
Figure 4B:
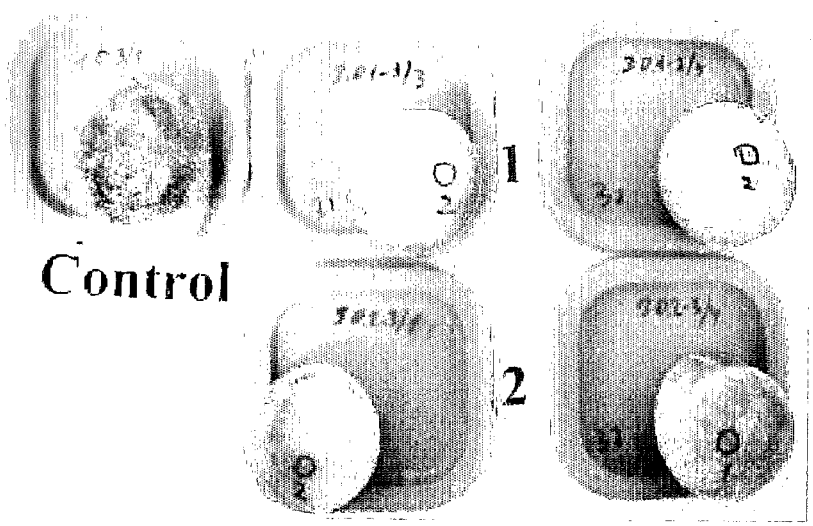

As shown in FIG. 4A, decay caused by *Rhizopus stolonifer* on peaches was suppressed by 2 ppm of *Eucalyptus citriodora* oil, following 3 h incubation, or by 0.4 ppm of *Eucalyptus citriodora* oil following 24 h incubation, followed by storage at 20° C. for 9 days, to a maximum extent of 100% and 85%, respectively. The effect of Thyme oil at a concentration of 0.4 ppm or 0.2 ppm on inhibition of development of decay in peaches inoculated with *Rhizopus stolonifer* and stored at 20° C. for 14 days is shown in FIG. 4B.

Example 5

**Low Doses of Mustard Essential Oil or Cinnamon Cassia Oil Significantly Reduce Decay Caused by Blue or Green Mould (*Penicillium italicum*) in Mandarins**

Mandarins (10 replicates of 10 fruits per container) were inoculated with *Penicillium italicum* (four inoculation sites with 10 μl suspension, $10^6$ spores/ml, on each fruit), incubated with Mustard essential oil (1-4 ppm) or Cinnamon cassia oil (20 ppm) in sealed containers for 3-24 hours and stored in the same slightly opened containers for up to 9 days at 4° C. or 20° C. Inoculated mandarins not treated with the essential oils were used as control.

Figure 5A:
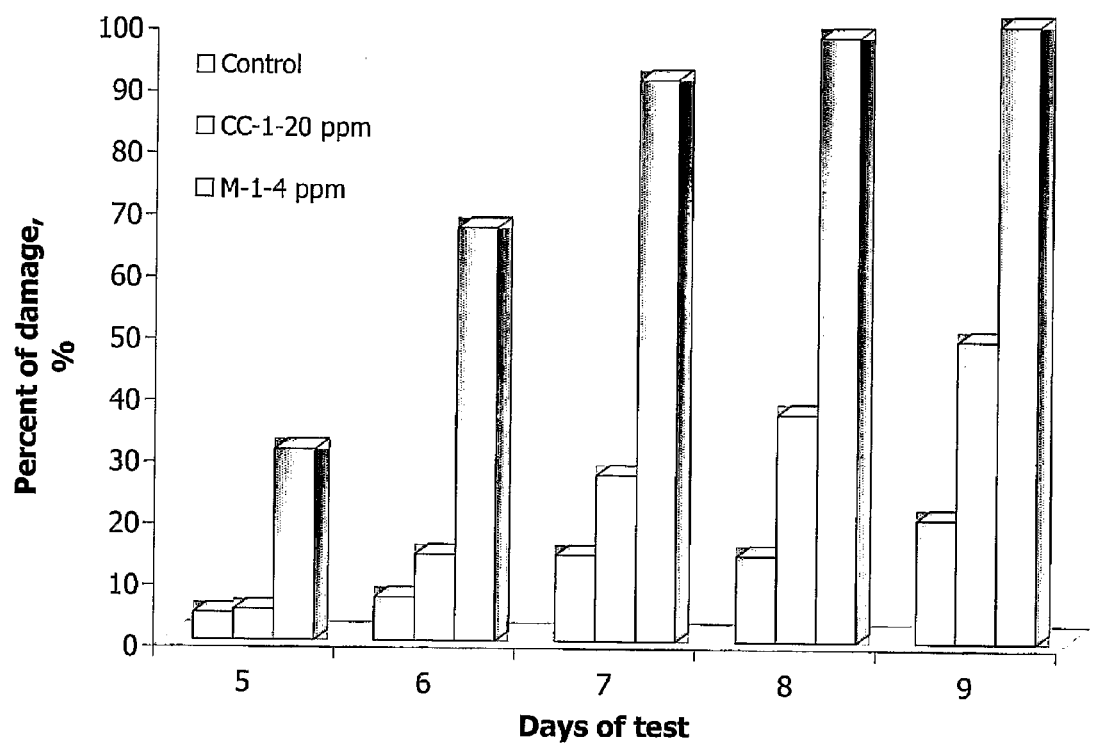
FIGS. 5A-5B show the effect of Mustard essential oil (M-1) or Cinnamon cassia oil (CC-1) on decay development in mandarins inoculated with Penicillium italicum ($10^6$ spores/ml).
Figure 5B:
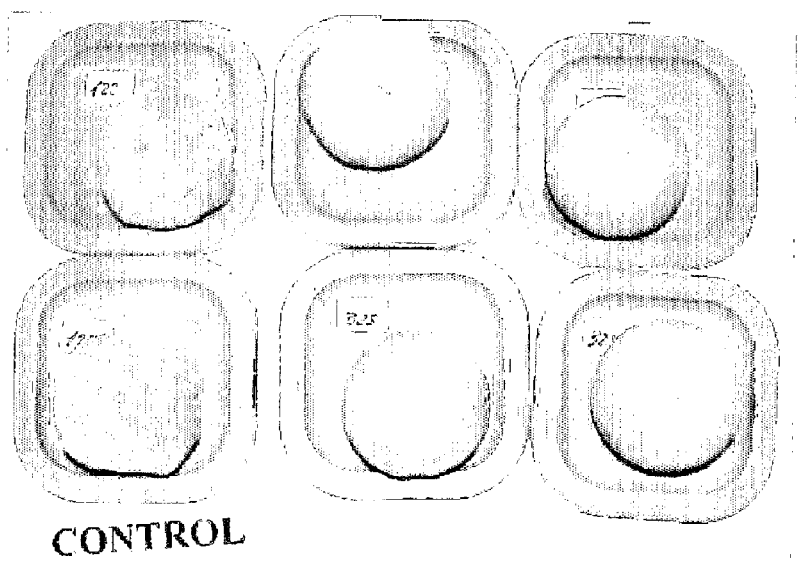

FIGS. 5A and 5B show the inhibitory effect of the essential oils on *Penicillium italicum* decay on mandarins. As shown in FIG. 5A, the decay was suppressed by 80% due to exposure to low doses of Mustard essential oil (4 ppm) at 20° C. followed by 9 days storage, and to the extent of 50% due to exposure to Cinnamon cassia oil under the same conditions. The effect of Mustard oil at a concentration of 4 ppm on development of decay in mandarins inoculated with *Penicillium italicum* and stored at 20° C. for 9 days, is shown in FIG. 5B.

Example 6

Quantification of the Marker Components in the Essential Oils

Different batches of Cinnamon cassia oil, Mustard essential oil, Thyme oil, Nutmeg oil and *Eucalyptus citriodora* oil from different producers were analysed by gas-chromatography (GC)-mass spectrometer (MS) analyses. A database containing chromatographic data of the selected essential oils has been compiled.

The identification of each tested oil component was verified and confirmed by mass spectral data Wiley 7N.I Library. Only components, which were present in the oils with relative amounts higher than 0.1% and validity above 90%, were taken into consideration. The quantification of marker components based on corresponding external reference standards has been done.

Figure 6:
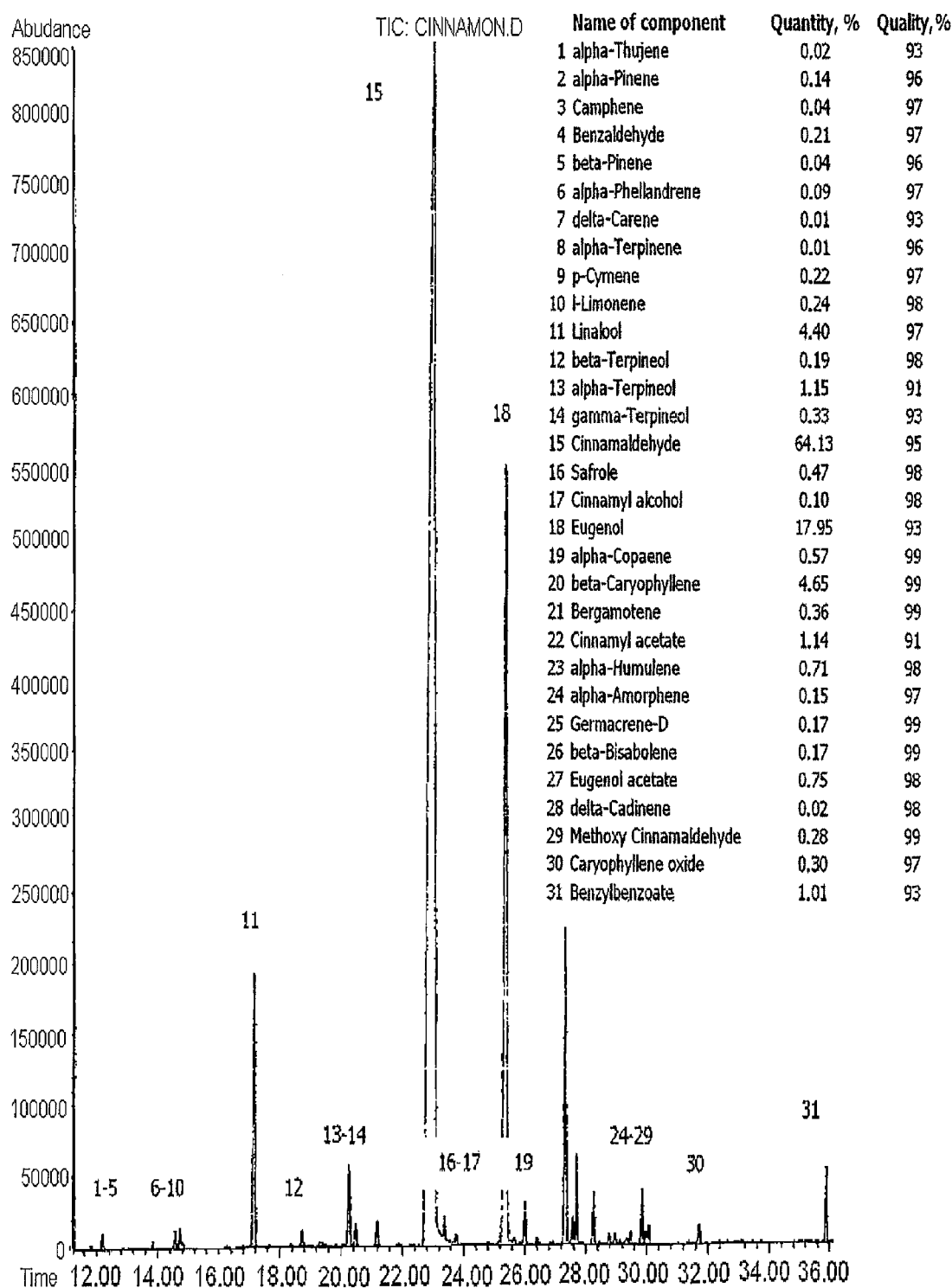
FIG. 6 is a GC-MS chromatogram of Cinnamon Cassia essential oil showing the ratio of the chemical its components and the reliability of each component's determination (Quality).

The analyses of samples of essential oils that were found to exhibit both the desired anti-fungal protection of harvested fruits and to pass the organoleptic testing, were compared, and the concentration range of the main fungicidal compounds, the marker components, in the essential oils, were established. The concentration ranges of the marker components of Cinnamon cassia oil, Thyme oil, Nutmeg oil, *Eucalyptus citriodora* oil and Mustard essential oil are shown in Tables 6-10, respectively, herein below. As an example, the GC-MS chromatogram of Cinnamon cassia oil indicating its main components is shown in FIG. 6.

Figure 7A:
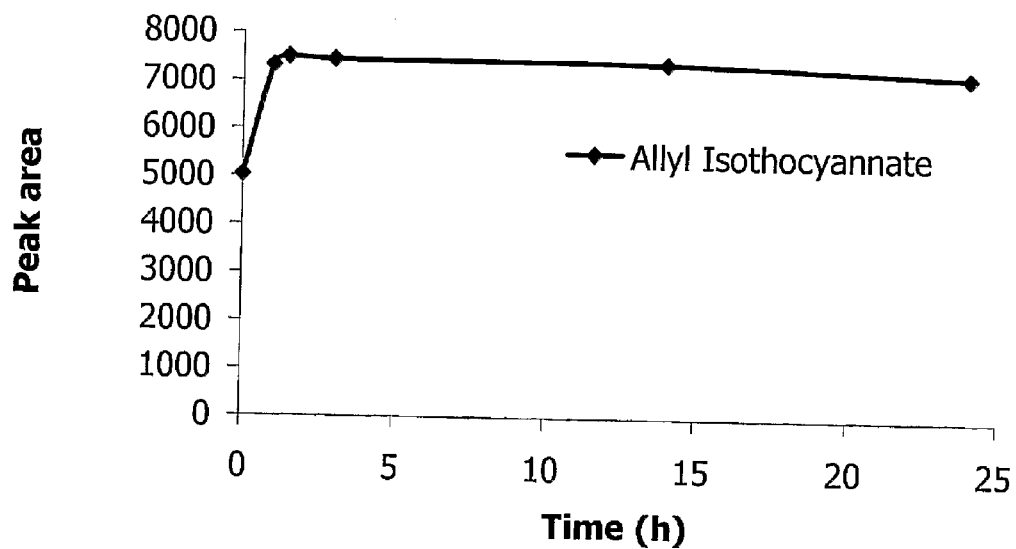
FIGS. 7A-7D are graphs showing the release profiles of main marker individual components of Mustard, Thyme, Nutmeg and Eucalyptus citriodora essential oils into vapor phase over a 24 hour period.
Figure 7B:
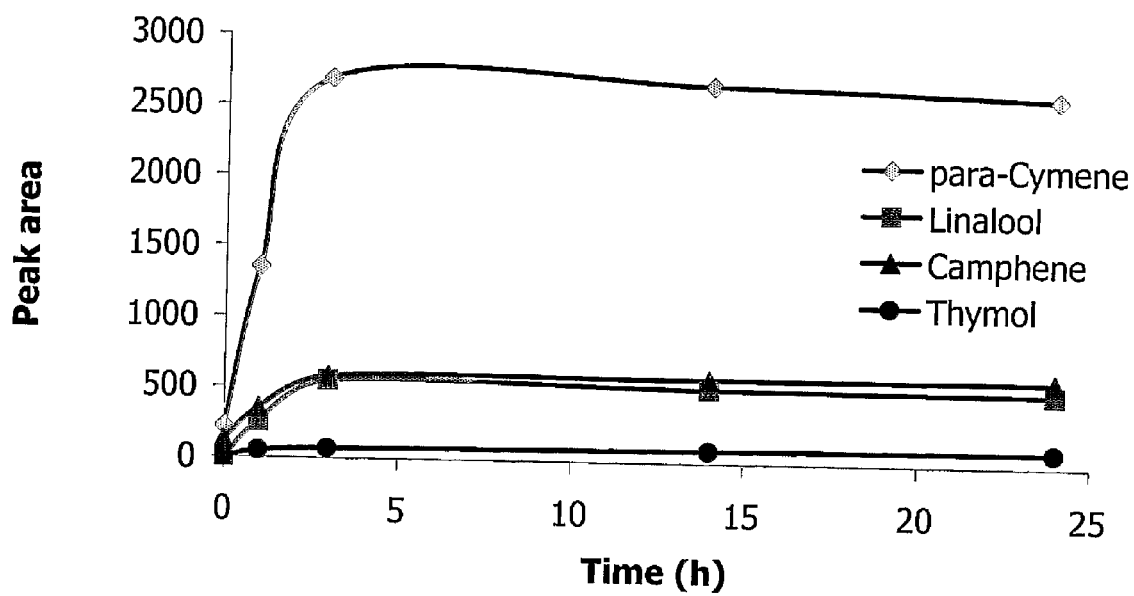
Figure 7C:
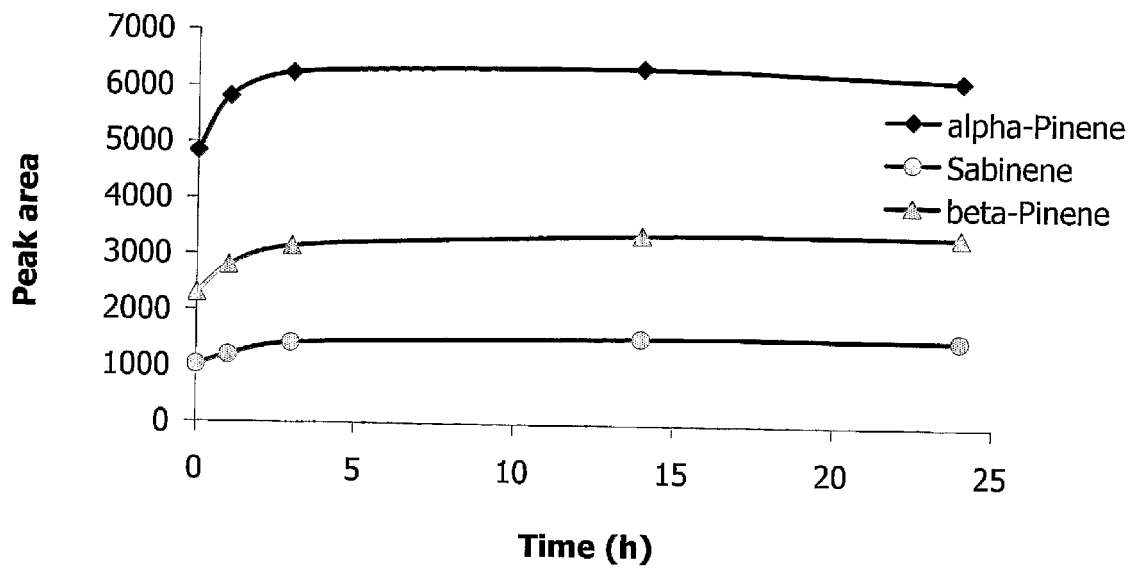
Figure 7D:
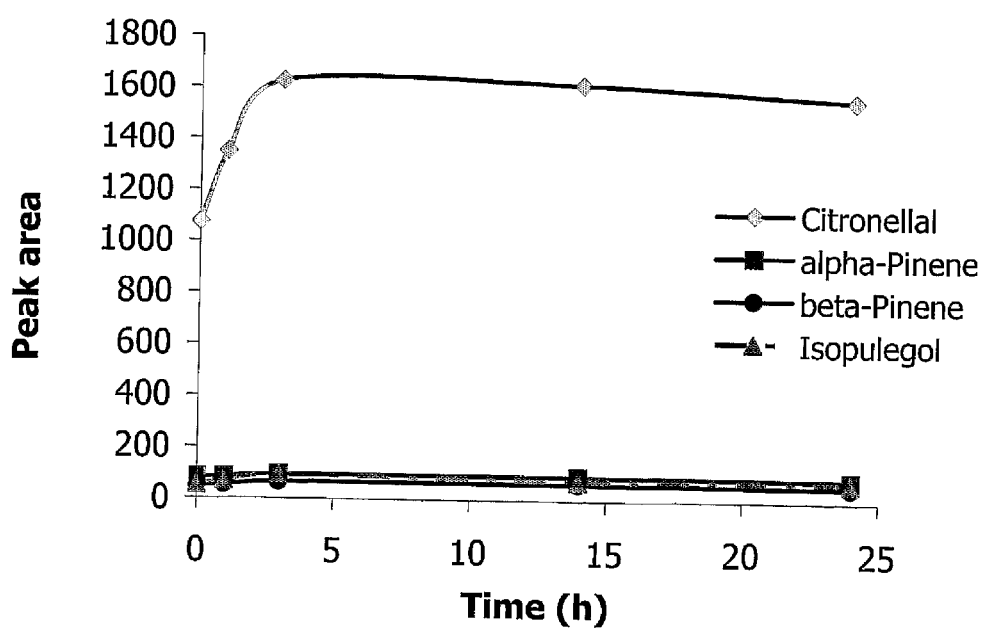

GC FID analysis was applied to determine the release profile into the vapor phase of marker individual components during a 24 hour period. As shown in FIG. 7A the saturation of the vapor phase due to the release of allyl isothiocyanate, a marker component of Mustard essential oil, was achieved in ~1.5 hours. Main marker components in the vapor phase of Thyme essential oil are presented in FIG. 7B. For all markers tested, saturation was achieved within 3 hours. FIG. 7C shows that saturation of vapor phase with the three main marker components of Nutmeg essential oil occurred within 2.5-3 hours, and according to FIG. 7D saturation of the vapor phase due to the release of citronellal, a main marker component of *Eucalyptus citriodora* essential oil, was also achieved in ~3.0 hours.

TABLE 6

Concentration range of marker components in Cinnamon *cassia* oil

| Name of chemical component | Concentration range, % |
| --- | --- |
| Cinnamic aldehyde | 60.0-98.0 |
| Cinnamyl acetate | 1.0-4.0 |
| Methoxycinnamic aldehyde | 0.5-15.0 |
| Linalool | 0.3-8.0 |
| beta-Caryophyllene | 0.2-6.0 |
| alpha-Pinene | 0.2-1.0 |
| Camphene | 0.1-0.7 |
| dl-Limonene | 0.2-1.5 |

TABLE 7

Concentration range of marker components in Thyme oil

| Name of chemical component | Concentration range, % |
| --- | --- |
| Thymol | 17.0-55.0 |
| Carvacrol | 0.5-5.5 |
| alpha-Pinene | 0.5-5.5 |
| 1,8-Cineol | 0.5-4.5 |
| alpha-Terpineol | 0.7-15.0 |
| Camphene | 0.5-6.5 |
| Linalool | 1.0-30.0 |
| p-Cymene | 7.0-12.0 |
| beta-Pinene | 0.2-1.5 |

TABLE 8

Concentration range of marker components in Nutmeg oil

| Name of chemical component | Concentration range, % |
| --- | --- |
| alpha-Pinene | 9.0-37.0 |
| beta-Pinene | 6.0-22.0 |
| Sabinene | 6.0-13.0 |
| Myristicin | 0.5-9.5 |
| Limonene | 1.0-9.5 |
| Terpinen-4-ol | 0.3-6.0 |

TABLE 9

Concentration range of marker components in *Eucalyptus citriodora* oil

| Name of chemical component | Concentration range, % |
| --- | --- |
| Citronellal | 43.0-82.0 |
| (+)-Citronellol | 2.0-5.0 |
| Isopulegol | 1.5-4.0 |
| Neoisopulegol | 0.2-4.0 |
| alpha-Pinene | 0.2-1.5 |
| beta-Pinene | 0.2-1.0 |

TABLE 10

Concentration range of marker components in Mustard essential oil

| Name of chemical component | Concentration range, % |
| --- | --- |
| Allyl isothiocyanate | 58.0-98.0 |
| 3-Butenyl isothiocyanate | 0.5-1.5 |
| Diallyl sulfide | 1.0-4.0 |

REFERENCES

Arras, G., Agabbio, M., Piga, A., D'hallewin, G., Gerasopoulos, D., Olympios, C. and Passam, H., 1995. Fungicide effect of volatile compounds of *Thymus capitatus* essential oil. Acta Horticulturae 379:593-600.

Ben-Arie, R., Zutkhi, Y., Sonego, L., Klein, J. 1991. Modified atmosphere packaging for long-term storage of astringent persimmons. Postharvest Biology and Technology, 1(2): 169-179.

Bennis, S., Chami, F., Chami, N., Bouchikhi, T., Remmal, 2004. A. surface alteration of *Saccharomyces cerevisiae* induced by thymol and eugenol. Lett Appl Microbiol. 38(6):454-8.

Caccioni, D. R. L. and Guizzardi, M., 1994. Inhibition of germination and growth of fruit and vegetable postharvest pathogenic fungi by essential oil components. J. Essential Oil Res. 6 (2):173-179.

Carlton, R. R., Waterman, P. G., Gray, A. I., Deans, S. G. 1992. The antifungal activity of the leaf gland volatile oil of sweet gale (*Myrica gale*) (Myricaceae). Chemoecology 3:55-59.

Carta, C., Moretti, M. D. L. and Peana, A. T., 1996. Activity of the oil *Silva officinalis* L. against *Botrytis cinerea*. J. Essential Oil Res. 8(4):399-404.

Cutler, H. G., Hill, R. A., Ward, B. G., Rohitha, B. H. and Stewart, A., 1996. Antimicrobial, insecticidal and medicinal properties of natural products, flavours and fragrances. Pp. 51-66 In: Biotechnologies for improved foods and flavours. G. R. Takeoka, R. Teranishi, P. J. Williams and A. Kobayashi (Eds.) American Chemical Society.

Deans, S. G., Svoboda, K. P., Gundiza, M., Brechany, E. Y. 1992. Essential oil profiles of several temperate and tropical aromatic plants: their antimicrobial and antioxidant activities. Acta Hortic, 306:229-232.

Lambert, R. J., Skandamis, P. N., Coote, P. J., Nychas, G. J. 2001. A study of the minimum inhibitory concentration and mode of action of oregano essential oil, thymol and carvacrol. J Appl Microbiol, 91: 453-462.

Palou, L., Smilanick, J. L., Usall, J, and Vinas, I. 2002, Control of postharvest blue and green molds of oranges by hot water sodium carbonate, and sodium bicarbonate. Plant Dis. 85:371-376.

Piccaglia, R., Marotti, M., Giovanelli, E., Deans, S. G., Eaglesham, E. 1993. Antibacterial and antioxidant properties of Meditarranean aromatic plants. Ind. Crops and Prod. 2:47-50.

Prusky, D., Eshel, D., Kobiler, I., Yakoby, N., Beno-Moualem, D., Ackerman, M., Zutkhi, Y. and Ben-Arie, R. (2001) Postharvest chlorine treatments for the control of the persimmon black spot disease caused by *Alternaria alternata*. Postharvest Biol. Technol. 22:271-277. Spotts, R. A., Cervantes, L. A. 1986. Populations, pathogenecity and benomyl resistance of *Botrytis* spp, *Penicillium* spp. And *Mucor piriformis* in packing houses. Plant Dis. 70:106-108.

Shamaila, M., W. D. Powrie, and B. J. Skura. 1992. Analysis of volatile compounds from strawberry fruits stored under modified atmosphere packaging (MAP). J. Food Sci. 57:1173-1176.

Wilson, C. L., Franklin, J. D., and Otto, B. E. 1987. Fruits volatiles inhibitory to *Monilinia fruticola* and *Botrytis cinerea*. Plant Disease 71:316-319.

Zambonelli, A., D'Aulerio, A. Z., Bianchi, A., Albasini, A. 1996. Journal of Phytopathology (Berlin); 144 (9-10): 491-494.

The invention claimed is:

1. A method for protecting harvested persimmons against *Alternaria alternata*, strawberries against *Botrytis cinerea*, or mandarins against *Penicillium italicum* or *Penicillium digitatum*, which comprises applying to said harvested persimmons, strawberries or mandarins a composition comprising Cinnamon cassia essential oil in a vaporized form in an amount sufficient to provide protection therefrom.

2. The method of claim 1, wherein said protection is for protecting persimmons against decay caused by *Alternaria alternata*.

3. The method of claim 1, wherein said protection is for protecting strawberries against decay caused by *Botrytis cinerea*.

4. The method of claim 1, wherein said protection is for protecting mandarins against decay caused by *Penicillium italicum* or *Penicillium digitatum*.

5. The method of claim 1, wherein said Cinnamon cassia oil comprises at least the following marker components: cinnamic aldehyde (60.0-98.0%), cinnamyl acetate (1.0-4.0%), methoxycinnamic aldehyde (0.5-15%), linalool (0.3-8.0%), beta-caryophyllene (0.2-6.0%), alpha-pinene (0.2-1.0%), camphene (0.1-0.7%) and dl-limonene (0.2-1.5%).

6. The method of claim 1 wherein said harvested persimmons, strawberries or mandarins are stored in a sealed container and are contacted with said vaporized composition.

7. The method of claim 1, wherein the application of Cinnamon cassia oil in vaporized form to the fruits does not show any organoleptic and phytotoxic impact on the fruits and does not have a detrimental effect on the fruits' aroma, flavor, or both.

8. A method for extending the shelf-life of harvested persimmons, strawberries or mandarins infected or liable to be infected by *Alternaria alternate, Botrytis cinerea, Penicillium italicum* or *Penicillium digitatum*, respectively, which comprises applying to the harvested persimmons, strawberries or mandarins a composition comprising Cinnamon cassia essential oil in a vaporized form in an amount sufficient to extend the shelf-life.

9. The method of claim 8, wherein said Cinnamon cassia essential oil comprises at least the following marker components: cinnamic aldehyde (60.0-98.00), cinnamyl acetate (1.0-4.0%), methoxycinnamic aldehyde (0.5-15%), linalool (0.3-8.0%), beta-caryophyllene (0.2-6.0%), alpha-pinene (0.2-1.0%), camphene (0.1-0.7%) and dl-limonene (0.2-1.5%).

10. The method of claim 8, wherein the application of Cinnamon cassia oil in vaporized form to the fruits does not show any organoleptic and/or phytotoxic impact on the fruits and does not have a detrimental effect on the fruits' aroma, flavor, or both.

* * * * *